United States Patent [19]

Barcza

[11] 4,175,091
[45] Nov. 20, 1979

[54] SUBSTITUTED 3,1-BENZAZASILINES

[75] Inventor: Sandor Barcza, West Orange, N.J.

[73] Assignee: Sandoz, Inc., E. Hanover, N.J.

[21] Appl. No.: 881,687

[22] Filed: Feb. 27, 1978

[51] Int. Cl.² .............................................. C07F 7/10
[52] U.S. Cl. ............................ 260/448.2 N; 548/110; 424/184
[58] Field of Search ................................ 260/448.2 N

[56] References Cited

U.S. PATENT DOCUMENTS

| | | | |
|---|---|---|---|
| 3,065,251 | 11/1962 | Jones et al. ................. | 260/448.2 N |
| 3,103,529 | 9/1963 | Tamborski et al. ........... | 260/448.2 N |
| 3,355,475 | 11/1967 | Baney ............................ | 260/448.2 N |
| 3,436,415 | 4/1969 | Finkbeiner et al. ........... | 260/448.2 N |
| 3,479,383 | 11/1969 | Klebe ............................ | 260/448.2 N |
| 3,793,253 | 2/1974 | Quiring et al. ............ | 260/448.2 N X |
| 3,803,194 | 4/1974 | Golitz et al. ................. | 260/448.2 N |

*Primary Examiner*—Paul F. Shaver
*Attorney, Agent, or Firm*—Gerald D. Sharkin; Robert S. Honor

[57] ABSTRACT

Compounds of the following structure

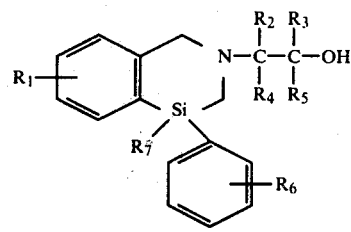

where
$R_1$ represents H or alkyl having 1–5 carbon atoms,
$R_2$, $R_3$, $R_4$ and $R_5$ each, independently represents H or alkyl having 1–2 carbon atoms
$R_6$ represents H, alkyl having 1–5 carbon atoms, halo, alkoxy having 1–5 carbon atoms or

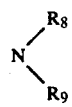

where
$R_8$ and $R_9$ each, independently, represent alkyl having 1–2 carbon atoms, and
$R_7$ represents alkyl having 1–5 carbon atoms, e.g., 1-(p-chlorophenyl)-1,4-dihydro-$\beta,\beta$,1-trimethyl-3,1-benzazasiline-3(2H)-ethanol, are prepared from corresponding oxazolo benzazasilanes by reduction with borohydride, and are useful as sleep inducers.

3 Claims, No Drawings

SUBSTITUTED 3,1-BENZAZASILINES

This invention relates to 3,1-benzazasiline-3-ethanol compounds of the formula

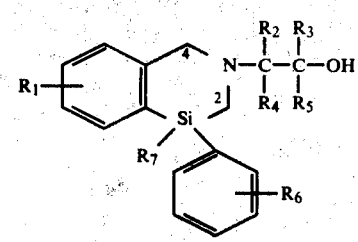

where
R$_1$ represents H or alkyl of 1-5 carbon atoms,
R$_2$, R$_3$, R$_4$ and R$_5$ each, independently, represent H or alkyl of 1-2 carbon atoms,
R$_6$ represents H, alkyl of 1-5 carbon atoms, halo having an atomic weight of about 19-36, alkoxy having 1-5 carbon atoms or

where
R$_8$ and R$_9$ each, independently, represent alkyl having 1-2 carbon atoms, and
R$_7$ represents alkyl having 1-5 carbon atoms.

When on the compounds (I) above the substituents are alkyl having 1-5 carbon atoms, they may be straight chain or branched and preferably contain 1-3 carbon atoms and more preferably represent methyl or ethyl, whereas when the alkyl substituents are said to have 1-2 carbon atoms, they preferably represent methyl. When the substituent R$_6$ represents said alkoxy, it may be straight chain or branched, preferably contains 1-3 carbon atoms and more preferably represents methoxy or ethoxy. Said halo represents more specifically chloro and fluoro.

The compounds (I) are prepared from compounds of the formula

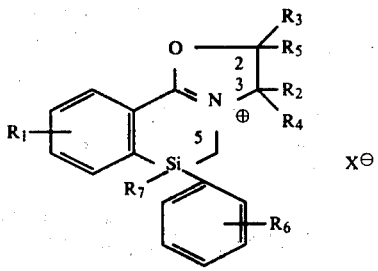

where
R$_1$-R$_7$ (i.e. including R$_8$ and R$_9$) are as indicated above, and
X represents a monovalent anion, e.g. chloride or bromide.

Compound (II) may be converted into compound (I) having corresponding substituents by treatment of the former in solvent with a reducing agent, such as an alkali metal borohydride, e.g. sodium or potassium borohydride or lithium aluminum hydride in aprotic solvent. The solvent used is conveniently water, but other solvents such as lower alkanols or ethers may also be utilized. The reaction mixture is preferably agitated to promote the reduction, and temperature of about −70° C. to about 150° C. may be used, preferably about 0° C. to 50° C. and most preferably about 20°–30° C. The reaction mixture is agitated for about 1-20 hours and cooled, distributed between an aqueous and an organic phase, and the organic phase obtained is washed, dried and concentrated using standard separation and purification techniques to yield the compounds (I).

Compounds (II) are prepared in a two step procedure. The first step involves lithiating a compound of the formula

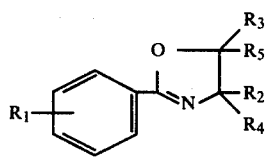

where
R$_1$-R$_5$ are as defined above,
with a compound of the formula $$R_{10}Li \qquad (IV)$$

where R$_{10}$ represents alkyl of 1–4 carbon atoms such as methyl, ethyl, isopropyl and the like,
in inert atmosphere, such as nitrogen gas, and inert solvent such as a hydrocarbon for example hexane or heptane, or an ether, e.g., diethyl ether or tetrahydrofuran, at a temperature of about −78° C. to +50° C., preferably at about −40° C. to 0° C., for about 0.5 to about 48 hours. The second step comprises treating the lithiated derivative of the compound of the formula (III) with a compound of the formula

where each Y, independently, represents halo, preferably chloro or bromo, at a temperature of about −80° C. to about 30° C. for about 0.5–48 hours. Although presence of solvent is not necessary, solvents such as hydrocarbons or ethers may be utilized in this second step if desired. The resulting product (II) may then be separated using standard techniques including extraction, crystallization and the like.

In none of the processes described above is the particular solvent or temperature of reaction critical, and variation in accordance with the knowledge and techniques of the ordinary, art-skilled chemist provides the products indicated.

To the extent not specifically indicated herein, it should be understood that the starting materials described are either known or may be prepared from known materials by methods analogous to processes described in the literature.

The compounds of formula I are useful because they possess pharmacological activity in animals. In particular, the compounds are useful as sleep inducers as indicated in standard tests, such as the 30 word adjective test basically as described by Irwin, S (Gordon Research Conference, Medicinal Chemistry, 1959), and Chen (Symposium on Sedative and Hypnotic Drugs, Williams and Wilkins, 1954) wherein the mice involved are administered 50–200 mg/kg of animal body weight of test compound I.P., and also as indicated in the test on mice regarding hexobarbital interaction, wherein anesthesia is induced by intravenous injection of 70 mg/kg of hexobarbital. Immediately after recovery, the test animals are administered about 200 mg/kg of test compound I.P., and reinduction of anesthesia results with compound having the indicated C.N.S. depressant effect. This method is a modification of that described by Winter et al. (J. Pharmacological Exp. Therapy 94: 7–11, 1948).

For this use, the compounds of formula (I) may be combined with a pharmaceutically acceptable carrier or adjuvant, and may be administered orally in such forms as tablets, capsules, elixirs, suspensions and the like, or parenterally in the form of sterile injectable solution or suspension. The dosage will vary depending on the compound employed and the mode of administration and treatment desired. However, in general, satisfactory results are obtained when a compound of formula I is administered at a daily dosage of from about 50 mg to about 200 mg per kilogram of animal body weight, conveniently given in divided doses 2 to 4 times a day or in sustained release form. For the larger mammals, the total daily dose is in the range of from about 250 mg to 1000 mg, and dosage forms, conveniently oral dose forms, suitable for internal use comprise from about 60 mg to about 500 mg of the active compound in intimate admixture with a solid or liquid pharmaceutically acceptable carrier or diluent.

Capsules containing 200 mg of active ingredient and 200 mg of lactose may be prepared by conventional techniques and are useful in inducing sleep at a dose of one capsule 2 to 4 times a day.

Furthermore, the compounds of formula (I) may be similarly administered in the form of their non-toxic pharmaceutically acceptable acid addition salts. Such salts possess the same order of activity as the free base, are readily prepared by reacting the base with an appropriate acid and accordingly are included within the scope of the invention. Representative of such salts are the mineral acid salts, such as the hydrochloride, hydrobromide, sulfate, phosphate and the like and the organic acid salts, such as the succinate, maleate, fumarate, acetate, p-toluenesulfonate, and the like.

EXAMPLE 1

1-(p-Chlorophenyl)-1,4-Dihydro-$\beta,\beta$,1-Trimethyl-3,1-Benzazasiline-3(2H)-Ethanol (a) 6-(p-chlorophenyl)-2,3-dihydro-3,3,6-trimethyloxazolo [3,2-c][3,1]benzazasilinium chloride To 44.2 g (252 m mol) of 4,4-dimethyl-4,5-dihydro-2-phenyl oxazole in 570 ml of absolute tetrahydrofuran under nitrogen is added at −50° C. to −45° C. with stirring 173 ml (277 m mole) of 1.6 N n-butyl lithium in hexane. Stirring is continued at that temperature for 1.5 hours except for a brief period at the end thereof to allow for warming to −35° C. The resulting mixture containing a yellow precipitate is re-cooled with dry ice-acetone and 61 g (255 m mol) of chloromethyl-p-chlorophenyl methyl chloro silane is added maintaining the temperature at between −78° C. and −55° C. The contents are allowed to warm to room temperature over a period of 3 hours and the resulting homogeneous solution is maintained at room temperature for an additional 20 hours. Addition of 1.2 ml of ether-ligroine (1:1) precipitates a semi-solid. The supernatent liquid is decanted and the residue is combined with 300 ml of methylene chloride and stirred briefly. The light slurry is filtered to remove lithium chloride and the mother liquor is concentrated in vacuo to 67.9 g of pink foam. Most of the foam is dissolved in cold water, sodium chloride solution (ca. 30%) is added, the aqueous phase is extracted with ethyl acetate to remove some impurities, and the remainder is extracted with chloroform. The chloroform phase is dried with sodium sulfate and evaporated. Addition of acetone and ether yields crystalline product having a melting point of 119°–121° C. Recrystallization from acetone-ethyl acetate (Ca. 1:1) provides product melting at 118°–120° C.

When the above process is carried out and in place of 4,4-dimethyl-4,5-dihydro-2-phenyl oxazole there is used a corresponding amount of (i) 4,5-dihydro-2-(p-tolyl) oxazole or (ii) 4,5-dihydro-5-methyl-2-phenyl oxazole, there is obtained:

(i) 6-(p-chlorophenyl)-2,3-dihydro-6,8-dimethyloxazolo [3,2-c][3,1]benzazasilinium chloride, or
(ii) 6-(p-chlorophenyl)-2,3-dihydro-2,6-dimethyloxazolo [3,2-c][3,1]benzazasilinium chloride, respectively.

When in place of chloromethyl-p-chlorophenyl methyl chloro silane in the above detailed procedure there is used a corresponding amount of (iii) chloromethyl-o-methoxyphenyl methyl chloro silane,
(iv) chloromethyl-p-dimethylaminophenyl methyl chloro silane or
(v) chloromethyl-p-tolyl methyl chloro silane, there is obtained
(iii) 2,3-dihydro-6-(o-methoxyphenyl-3,3,6-trimethyloxazolo [3,2-c][3,1]benzazasilinium chloride,
(iv) 2,3-dihydro-6-(p-dimethylaminophenyl)-3,3,6-trimethyloxazolo [3,2-c][3,1]benzazasilinium chloride or
(v) dihydro-6-(p-tolyl)-3,3,6-trimethyl-oxazolo [3,2-c][3,1]benzazasilinium chloride, respectively.

(b) 1-(p-chlorophenyl)-1,4-dihydro-$\beta,\beta$,1-trimethyl-3,1-benzazasiline-3(2H)-ethanol)

The crude benzazasilinium chloride (34.8 g., 92 m mol) obtained in part (a) above is dissolved in 20 ml. of water and 10 ml. of methanol and the solution is added with stirring to 52.6 g. (1.38 mol) of sodium borohydride in 500 ml. of peroxide free 1,2-dimethoxyethane between 20° and 30° C. After stirring 16 hours, the reaction mixture is poured into an ice-toluene-sodium potassium tartrate-water mixture. The organic phase is washed with water, dried with sodium sulfate and concentrated to an oil. The latter is passed in chloroform through a short silica gel column. The main portion of the effluent is concentrated to yield the title product as an oil. When dissolved in acetone and upon adding 2 g. of HCl gas with cooling and addition of ethyl ether, the free base is converted into the hydrochloride salt. The resultant crystals (m.p. 197°–198° C.) are recrystallized from ethanol-acetone-ether (ca. 1:2:5) and methanol-acetone-ether (ca. 1:3:5) and then acetone to obtain the purified salt (199°–200.5° C.).

When the above detailed process is carried out and in place of 6-(p-chlorophenyl-2,3-dihydro-3,3,6-trimethyloxazolo [3,2-c][3,1]benzazasilinium chloride there is used
(i) 6-(p-chlorophenyl-2,3-dihydro-6,8-dimethyloxazolo [3,2-c][3,1]benzazasilinium chloride,
(ii) 6-(p-chlorophenyl)-2,3-dihydro-2,6-dimethyloxazolo [3,2-c][3,1]benzazasilinium chloride,
(iii) 2,3-dihydro-6-(o-methoxyphenyl)-3,3,6-trimethyloxazolo [3,2-c][3,1]benzazasilinium chloride,
(iv) 2,3-dihydro-6-(p-dimethylaminophenyl)-3,3,6-trimethyloxazolo [3,2-c][3,1]benzazasilinium chloride, or
(v) 2,3-dihydro-6-(p-tolyl)-3,3,6-trimethyl oxazolo [3,2-c][3,1]benzazasilinium chloride, there is obtained
(i) 1-(p-chlorophenyl)-1,7-dimethyl-1,4-dihydro-3,1-benzazasiline-3(2H)-ethanol,
(ii) 1-(p-chlorophenyl)-α,1-dimethyl-1,4-dihydro-3,1-benzazasiline-3(2H)-ethanol,
(iii) 1-(o-methoxyphenyl)-1,4-dihydro-β,β,1-trimethyl-3,1-benzazasiline-3(2H)-ethanol,
(iv) 1-(p-dimethylaminophenyl)-1,4-dihydro-β,β,1-trimethyl-3,1-benzazasiline-3(2H)-ethanol, or,
(v) 1-(p-tolyl)-1,4-dihydro-β,β,1-trimethyl-3,1-benzazasiline-3(2H)-ethanol, respectively.

What is claimed is:

1. A compound of the formula

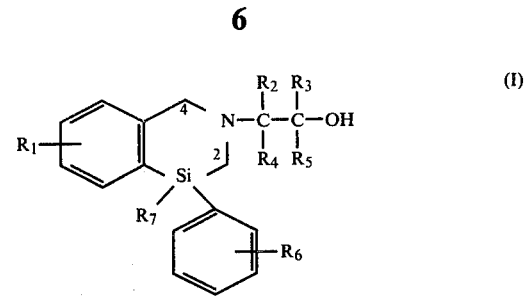

where
$R_1$ represents H or alkyl of 1–5 carbon atoms,
$R_2$, $R_3$, $R_4$ and $R_5$ each, independently, represent H or alkyl of 1–2 carbon atoms,
$R_6$ represents H, alkyl of 1–5 carbon atoms, halo having an atomic weight of about 19–36, alkoxy having 1–5 carbon atoms, or

where
$R_8$ and $R_9$ each, independently, represent alkyl having 1–2 carbon atoms, and
$R_7$ represents alkyl having 1–5 carbon atoms.

2. A compound of claim 1 wherein $R_6$ is said halo.

3. The compound of claim 2 which is 1-(p-chlorophenyl)-1,4-dihydro-β,β,1-trimethyl-3,1-benzazasiline-3(2H)-ethanol.

* * * * *